United States Patent [19]
Kozinski
[11] 4,185,022
[45] Jan. 22, 1980

[54] FURFURYL ALCOHOL PRODUCTION PROCESS

[75] Inventor: Allen A. Kozinski, Crystal Lake, Ill.
[73] Assignee: The Quaker Oats Company, Chicago, Ill.

[21] Appl. No.: 818,440
[22] Filed: Jul. 25, 1977
[51] Int. Cl.² .............................................. C07F 307/44
[52] U.S. Cl. .................................................. 260/347.8
[58] Field of Search ...................................... 260/347.8

[56] References Cited

U.S. PATENT DOCUMENTS

| | | | |
|---|---|---|---|
| 1,739,919 | 12/1929 | Ricard et al. | 260/347.8 |
| 2,071,704 | 2/1937 | Normann et al. | 260/347.8 |
| 2,754,304 | 7/1956 | Swadesh | 260/347.8 |
| 2,947,707 | 8/1960 | Wells | 252/419 |
| 3,177,258 | 4/1965 | Rylander et al. | 260/347.8 X |
| 3,953,524 | 4/1976 | Steiner | 260/347.8 X |

*Primary Examiner*—Richard Raymond
*Attorney, Agent, or Firm*—Joseph P. O'Halloran

[57] ABSTRACT

A furfuryl alcohol production process having improved catalyst productivity is disclosed. The present method comprises utilization of an improved catalyst comprising an inert carrier having at least 60 square meters per gram surface area, and containing a mixture of reduced copper and sodium silicate in which the sodium silicate in the mixture contains between 5 and 20 percent on a dry weight basis, and in which the overall catalyst mixture has at least 8 percent copper metal, but not more than 25 percent, when in reduced form.

3 Claims, No Drawings

FURFURYL ALCOHOL PRODUCTION PROCESS

BACKGROUND OF THE INVENTION

U.S. Pat. No. 2,754,304 issued July 10, 1956 to Samuel Swadesh disclosed that the production of furfuryl alcohol by the reduction of furfural using a catalyst consisting essentially of an intimate mixture of reduced copper and anhydrous sodium silicate. U.S. Pat. No. 2,947,707 issued to Preston A. Wells discloses a regeneration process wherein a copper oxide-sodium silicate catalyst is regenerated in an involved multi-step process.

The present invention relates to a process which is much improved with respect to this traditional process, particularly with respect to productivity based on pounds of furfuryl alcohol produced per pound of catalyst, but more significantly with respect to pounds of furfuryl alcohol produced with respect to pounds of active copper metal employed. The productivity improvement which is achieved in accordance with the present invention is important because of several significant aspects. For example, the presently employed regeneration processes can incur approximately 10–15 percent catalyst loss per regeneration cycle due to dusting and mechanical losses during handling. Also, because of the substantially lower level of copper metal present in the method of the present invention, substantially lower exotherms are encountered during regeneration procedures, resulting in more easily controlled regenerations, and in a simple in situ regeneration procedure.

In addition, the improvement of productivity using the lower metal-level catalyst in accordance with the present invention therefore also achieves lower cost inasmuch as catalyst costs are based to a major extent on the concentration of metal present in the catalyst.

Another advantage of the present invention is that an extremely high quality relatively pure furfuryl alcohol is produced directly from furfural in one step in the vapor phase process in accordance with the present invention.

SUMMARY OF THE INVENTION

In accordance with the present invention relatively pure furfuryl alcohol is produced directly from furfural in a process comprising passing furfural in the vapor phase and in the presence of a stoichiometric excess of free hydrogen at a temperature between 120°–160° C. over a catalyst consisting essentially of reduced copper and anhydrous sodium silicate on a high surface area support, the silicate constituting between 5–20 percent by weight of the reduced copper-anhydrous sodium silicate portion, the copper constituting more than 8 percent but not more than 25 percent of the overall catalyst mixture.

The high surface area carrier is a neutral or alkaline inorganic high surface area material having at least 60 square meters per gram prior to the deposition of the copper-sodium silicate components thereon. Typical neutral or alkaline inorganic supports meeting the requirements in accordance with the present invention include pumice, silica gel, silica quartz, and neutral aluminas, for example, but this list is not intended to exclude other supports which meet the requirements set forth herein. The surface area can be determined in any conventional manner, the method of Brunauer, Emmett & Teller (the BET method) utilizing nitrogen absorption being the preferred method to determine surface area.

The surface area of the copper-sodium silicate method of Swadesh in U.S. Pat. No. 2,754,304 typically is in the 3–5 meter square per gram range. In accordance with the present invention, the surface area of the inert carrier prior to deposition of the copper-sodium silicate portion thereon, has at least 60 square meters per gram.

The catalysts of the present invention are prepared, generally speaking, by admixing a neutral or alkaline (pH greater than 7) solid having the high surface area in accordance with the previous discussion, with a solution of sodium silicate and copper carbonate. The copper compound is preferably one including anions which do not generate strong acids or which are difficult to remove from the carrier. For example, copper chloride is preferably avoided. Copper carbonate is a preferred material. It is preferred that the copper metal constitute between 10 and 20 percent of the weight of the overall catalyst.

The aqueous admixture of carrier and copper compound-sodium silicate solution is stripped under vacuum using minimal heat to produce a carrier-copper compound-sodium silicate initimate mixture. The dry mixture is heated to decompose the copper compound to copper oxide, and the resulting catalyst is charged to a conventional recycle fixed bed reactor such as the type described in U.S. Pat. No. 2,754,304 the description of which therein is incorporated by reference thereto therein, and the copper oxide is then reduced in a stream of nitrogen having hydrogen therein, or under carefully controlled conditions by carefully introducing hydrogen to the catalyst in an inert atmosphere, or in a hydrogen atmosphere after all oxygen has been purged from the system.

In the following examples, specific preferred embodiments in accordance with the present invention will be disclosed, and the invention will be disclosed generally, as well. All temperatures are expressed in degrees centigrade, and all percents are in percent by weight based on the weight of the material or mixture then referred to. All parts are also in parts by weight.

EXAMPLE 1

The purpose of this Example is to illustrate the preparation of a preferred catalyst in accordance with the present invention. A sodium silicate-copper carbonate aqueous solution is admixed with pumice having an initial surface area of at least 60 square meters per gram (as determined by the BET test) and upon flashing of the aqueous solvent therefrom by reduced pressure, the remaining dry admixture is found by analysis to contain 21.88 percent copper carbonate, 1.96 percent sodium silicate, 76.16 percent pumice. This admixture is heated to an elevated temperature sufficient to reduce the copper carbonate to copper oxide, at which point it is activated by passage thereover, at a temperature in the range 150°–400° C., and a hydrogen or hydrogen-nitrogen mixture until the copper oxide has been reduced to metallic copper. In accordance with the embodiment of this particular Example, the resulting catalyst, after the reduction, has approximately 12.5 percent copper metal, 2.2 percent sodium silicate, and 85.3 percent pumice. The ratio between the copper metal and sodium silicate is approximately 85–15, after reduction.

EXAMPLE 2

The purpose of this Example is to illustrate a preferred method for direct reduction of furfural to furfuryl alcohol; and to povide a comparison of the result obtained when using the conventional copper oxide-sodium silicate catalyst (unsupported) with the improved method in accordance with the present invention utilizing the relatively low concentration of copper-sodium silicate on the high surface area carrier.

Furfural is vaporized at a rate of 50 parts per hour, continuously mixed with a quantity of hydrogen greatly in excess of that theoretically needed to reduce all the furfural to furfuryl alcohol, and the resulting mixture is then passed through a converter containing a catalyst in accordance with the present invention (Test A) and, in a separate test, through a converter containing a catalyst in accordance with U.S. Pat. No. 2,754,304, Example 2 (Test B). The converter is maintained at a temperature from about 120° C. to about 150° C. From the converter the vapors pass through a condensate where the hydrogenation product consisting almost entirely of furfuryl alcohol, a small amount of unchanged furfural together with traces of water and methyl furan, are condensed and removed from the system. Since a large amount of hydrogen is used, the excess hydrogen is recycled for efficient operation. This is accomplished by mixing the hydrogen which is to be recycled with furfural vapors and "make-up" hydrogen and again passing the entire resulting mixture through the converter.

These tests are conducted, for the present comparison, utilizing a converter which consists of a stainless steel tube approximately 0.5 inches in diameter, and a quantity of catalyst sufficient to provide approximately a 6" deep fixed bed therein. This so-called "mini-reactor" is employed in these two substantially identical test runs. The only difference between the operating parameters in the two respective runs is that Test A utilizes the catalyst produced in accordance with the method described in Example 1 herein, thus illustrating the process of the present invention, and Test B utilizes the catalyst produced in accordance with Example 1 of Swadesh Pat. No. 2,754,304, thus illustrating the process of the prior art.

The results of these tests are summarized in Table I herein. The test runs are continued until the furfuryl alcohol product of the respective test contains an increased level of furfural such that the then-produced product would not meet the usual commercial specifications for furfuryl alcohol, namely, the furfural content begins to exceed 0.5 percent of the product.

The quantity of furfuryl alcohol produced up to that point of the test run is then determined, and the productivity (based both on parts of furfuryl alcohol produced per weight of catalyst, and parts of furfuryl alcohol produced per weight of active catalyst metal) is determined and tabulated in respective columns in Table I.

TABLE I

| Test | Productivity Based on Gross Catalyst | Productivity per parts of Active Metal |
|---|---|---|
| A (in accordance with invention) | 21 parts/parts catalyst | 170 parts/parts copper |
| B (in accordance with prior art) | 6 parts/parts catalyst | 9.3 parts/parts copper |

It is noted that in the test in accordance with the present invention the furfuryl alcohol produced contained approximately 98 percent furfuryl alcohol, the balance being tetrahydrofurfuryl alcohol and methylfuryl ketone, with no indentifiable furfural for most of the test, whereas the test in accordance with the prior art produced approximately 96 percent furfuryl alcohol containing about 0.1 to 0.2 percent furfural for most of the runs.

EXAMPLE 3

The purpose of this Example is to illustrate the comparative regenerations of the respective catalysts. Each of the respective catalyst beds, after completion of the runs referred to in Example 2, is subjected to a stream of nitrogen and steam for the purpose of stripping from the bed volatile materials which would add to an excess of exotherm upon air or oxygen regeneration. Each of the beds is then subjected to identical streams of nitrogen and gradually molecular oxygen is added to provide about 1½ volume percent of molecular oxygen in the mass under conditions whereby the temperature of the mass is increased gradually (but not exceeding the sintering temperature) until all of the copper is substantially completely converted to copper oxide. The bed utilizing the catalyst of the present invention (that produced in Test A) is observed to have substantially no exotherm during this step. The bed using the catalyst in accordance with the prior art (Test B) is observed to have relatively sharp exotherms during this procedure. The presence of sharp exotherms leads to uncontrolled exotherm as a consequence of the localized burning of the carbonaceous material, thus decreasing the quality of the resulting regenerated catalyst. In accordance with the method of the present invention, however, the resulting regenerated catalyst is found to return to high quality and high productivity after regeneration.

DISCUSSION

It is apparent from the Examples that the method of the present invention provides a process for producing furfuryl alcohol directly from furfural by the direct hydrogenation of furfural under conditions, and using a catalyst, which results in productivities vastly superior to those achieved using the traditional copper-sodium silicate catalyst.

Although a specific embodiment presently regarded as the best mode has been disclosed herein in detail, these Examples are not intended to be limiting with respect to the scope of the invention. For example, the method shows the separation of the catalyst by depositing the copper-sodium silicate portion thereof from an aqueous solution. In addition, the catalyst can be prepared by any other method, for example, by intimately admixing the high surface area material with a liquid suspension of insoluble copper compounds and sodium silicate with subsequent flashing of the liquid therefrom to produce an intimate mixture of copper compounds, such as oxide or hydroxide, and sodium silicate, and carrier.

Thus the scope of the invention is intended to be limited only by the claims appended hereto.

I claim:

1. A process for producing relatively pure furfuryl alcohol directly from furfural which comprises passing furfural in the vapor phase in the presence of hydrogen at a temperature between 120°–160° C. over a catalyst consisting essentially of a neutral or alkaline inorganic carrier having high surface area of at least 60 square meters per gram prior to deposition of copper-sodium silicate components thereon, and containing a copper-sodium silicate deposited therewith, the amount of silicate in the copper-sodium silicate constituting between about 5 and 20 percent on a dry weight basis, the amount of copper in the overall catalyst mixture consisting of at least 8 percent by weight thereof, but not more than 25 percent, when reduced.

2. The method of claim 1 in which the copper metal constitutes between 10 and 20 percent of the overall catalyst by weight.

3. The method of claim 1 in which the carrier is pumice.

* * * * *